United States Patent
Li et al.

(10) Patent No.: US 8,403,974 B2
(45) Date of Patent: Mar. 26, 2013

(54) MEDICAL WARMING SYSTEM WITH NANO-THICKNESS HEATING ELEMENT

(75) Inventors: Geng Li, Hong Kong (HK); Cho Yee Joey Chow, Hong Kong (HK); Chih Lin I, Hong Kong (HK); Edward S. Yang, Hong Kong (HK)

(73) Assignee: Advanced Materials Enterprises Company Limited, Hong Kong (HK)

( * ) Notice: Subject to any disclaimer, the term of this patent is extended or adjusted under 35 U.S.C. 154(b) by 747 days.

(21) Appl. No.: 12/507,059

(22) Filed: Jul. 21, 2009

(65) Prior Publication Data

US 2010/0023098 A1   Jan. 28, 2010

Related U.S. Application Data

(60) Provisional application No. 61/083,076, filed on Jul. 23, 2008.

(51) Int. Cl.
*A61F 7/00* (2006.01)
*H05B 3/16* (2006.01)
*H05B 3/10* (2006.01)

(52) U.S. Cl. .......... 607/96; 607/108; 219/217; 219/543; 219/553; 5/601

(58) Field of Classification Search ............ 607/96–102, 607/108–112; 601/15; 219/520, 528, 385, 219/443.1–448.19, 452.12, 460.1–462.1, 219/468.1–468.2, 211–212, 553, 543, 217; 5/600–601; 252/518.1–521.6; 427/2.1, 450, 427/455, 124, 586, 250
See application file for complete search history.

(56) References Cited

U.S. PATENT DOCUMENTS

| 4,952,783 | A  | * | 8/1990 | Aufderheide et al. ........ 219/528 |
| 5,964,723 | A  |   | 10/1999 | Augustine |
| 2007/0251007 | A1 | * | 11/2007 | Simmerer et al. ................ 5/601 |
| 2008/0077201 | A1 |   | 3/2008 | Levinson et al. |
| 2008/0190912 | A1 | * | 8/2008 | Yeung et al. ................ 219/443.1 |
| 2009/0177257 | A1 | * | 7/2009 | Khodak et al. .................. 607/96 |
| 2010/0012643 | A1 | * | 1/2010 | Li et al. ........................ 219/387 |

FOREIGN PATENT DOCUMENTS

WO    2008/062193    5/2008

OTHER PUBLICATIONS

Search report for the European Patent Application No. 09799984.1.
First Office Action of Chinese Patent Application No. 200980128547.7.

* cited by examiner

*Primary Examiner* — Linda Dvorak
*Assistant Examiner* — Adam Avigan

(57) ABSTRACT

A medical warming system includes a plurality of heating elements respectively adapted to be disposed closed to various parts of a plurality of patients' bodies, a first group of sensors disposed at the proximity of the heating elements and configured for measuring the temperatures of the heating elements, a second group of sensors adapted to be disposed at the various parts of the patients' bodies and configured for measuring the temperatures of the various parts of the patients' bodies, and a controller being in communication with the first group and the second group of sensors. The controller is configured for receiving temperature data from the sensors and controlling the temperature of each heating element accordingly. Each heating element includes a conductive layer made from a nano-thickness material.

21 Claims, 11 Drawing Sheets

MEDICAL WARMING SYSTEM WITH NANO-THICKNESS HEATING ELEMENT

CROSS-REFERENCE TO RELATED APPLICATIONS

This application claims the benefit of U.S. Provisional Application No. 61/083,076, filed on Jul. 23, 2008; the contents of which is hereby incorporated by reference.

FIELD OF THE PATENT APPLICATION

The present invention generally relates to medical warming technologies and more particularly to a medical warming system with a nano-thickness heating element.

BACKGROUND

Maintaining patient body temperature at an acceptable level is very important in many medical procedures. For example, if a patient's body temperature drops below the normal level during a surgery, the patient could possibly develop hypothermia, which can prolong or complicate the patent's recovery. If a patient is kept warm before, during and after surgeries, post-operative problems such as excessive bleeding, infection and etc. can be minimized.

To maintain a patient's body temperature, a variety of medical warming devices have been designed. Some of these medical warming devices require wires for transmitting temperature data and control signals. Some of these medical warming devices require manual control of heating elements. Some of these medical warming devices sense only the temperature of the heating elements rather than the accurate temperature of the patient's body. Fast heating response with temperature control at high accuracy is generally desired in a medical warming device. The above mentioned medical warming devices generally cannot satisfactorily achieve these purposes.

In medical procedures, another essential operational condition is that a medical warming device does not generate magnetic interference to other equipments. Conventional heating methods such as metal wire heating, metal coil heating and induction heating all induce magnetic field through operation and thus create magnetic interference to other equipments.

SUMMARY

This patent application is directed to a medical warming system having a plurality of heating elements respectively adapted to be disposed closed to various parts of a plurality of patients' bodies, a first group of sensors disposed at the proximity of the heating elements and configured for measuring the temperatures of the heating elements, a second group of sensors adapted to be disposed at the various parts of the patients' bodies and configured for measuring the temperatures of the various parts of the patients' bodies, and a controller being in communication with the first group and the second group of sensors. The controller is configured for receiving temperature data from the sensors and controlling the temperature of each heating element accordingly. Each heating element includes a conductive layer made from a nano-thickness material.

The medical warming system may further include a power control board being in communication with the heating elements and configured for controlling the electric power driving the heating elements. The controller may be configured to control the power control board to individually adjust the electric power provided to each heating element independently from each other. The controller may be configured to control the temperature of each heating element according to a predetermined target temperature and the temperature of a corresponding part of the patient's body that is measured by a corresponding sensor in the second group of sensors disposed at the proximity of the corresponding part of the patient's body. The controller may be configured to increase the electric power provided to a heating element if the temperature of a corresponding part of the patient's body is lower than the target temperature, to reduce the electric power provided to the heating element if the temperature of the corresponding part of the patient's body is higher than the target temperature, and to maintain the electric power provided to the heating element if the temperature of the corresponding part of the patient's body is equal to the target temperature. The controller may be physically located at a centralized location, and the heating elements, the first group of sensors and the second group of sensors may be located remotely to the centralized location.

The controller may be configured to control the rate of temperature increase of each heating element according to a predetermined setting.

The medical warming system may further include a storage module. The storage module may be configured for storing settings of the system for operating the system at particular patients or under particular conditions. The controller may be configured to load system settings from the storage module and control the heating elements according to the settings.

The nano-thickness material may be non-magnetic and configured for generating heat when driven by a direct current power supply.

Each sensor in the first group and the second groups of sensors may include a working sensor and a reference sensor. The controller may be configured to compare the readings from the working sensor and the reference sensor and thereby to determine whether the sensor is working properly.

Communications between the controller and the sensors may be wireless.

DETAILED DESCRIPTION

Reference will now be made in detail to a preferred embodiment of the medical warming system with a nano-thickness heating element disclosed in the present patent application, examples of which are also provided in the following description. Exemplary embodiments of the medical warming system disclosed in the present patent application are described in detail, although it will be apparent to those skilled in the relevant art that some features that are not particularly important to an understanding of the medical warming system with a nano-thickness heating element may not be shown for the sake of clarity.

Furthermore, it should be understood that the medical warming system disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1A:
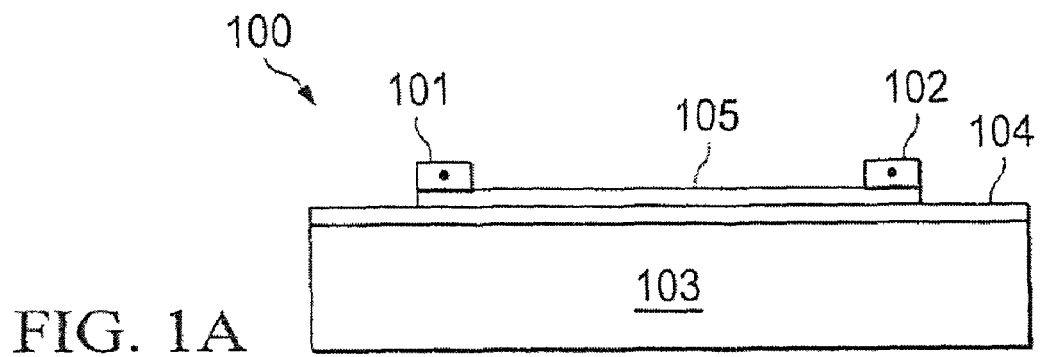
FIG. 1A is a side view of a heating element of a medical warming system according to an embodiment of the present patent application.
Figure 1B:
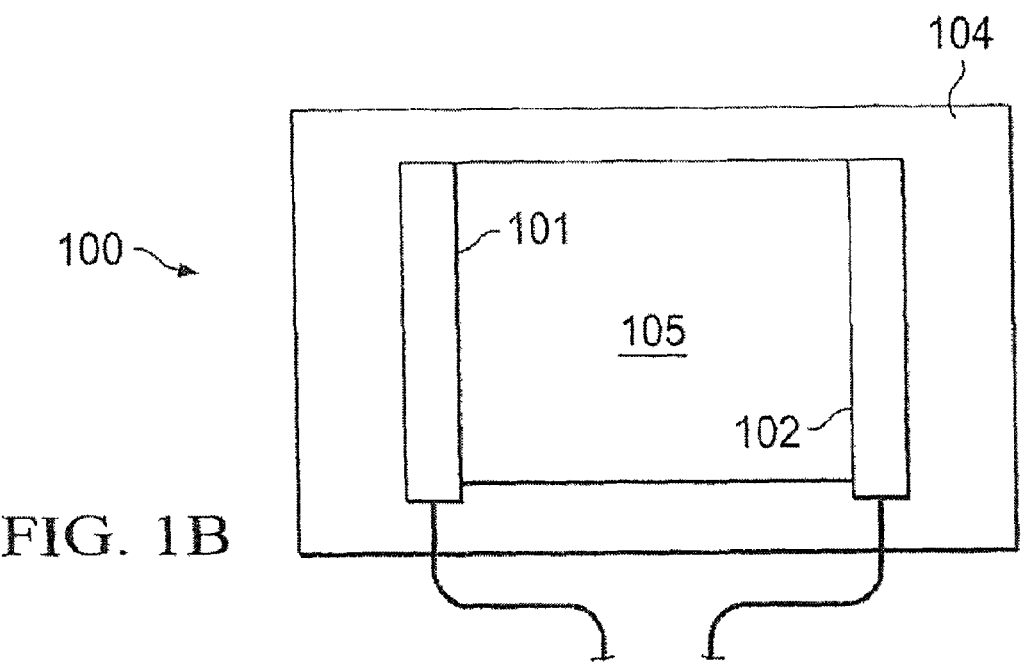
FIG. 1B is a top view of the heating element depicted in FIG. 1A.

FIG. 1A is a side view of a heating element 100 of a medical warming system according to an embodiment of the present patent application. FIG. 1B is a top view of the heating element depicted in FIG. 1A. The heating element 100 is configured to contact human body so as to transfer heat thereto. The heating element 100 includes a substrate 103, an insulating layer 104 disposed on the substrate 103, a conductive layer 105 disposed on the insulating layer 104, and two electrodes 101 and 102 respectively disposed on the insulating layer 104. The substrate 103 is made of glass, ceramic glass, or plastics (for example high temperature plastics). The insulating layer 104 and the conductive layer 105 may respectively include 8-12 layers, each of which is 60 nm-70 nm thick. The total thicknesses of the insulating layer 104 and the conductive layer 105 is respectively 720 nm-840 nm. A nano-thickness structure is to improve the adhesion bonding of the layers onto the substrate. The material composition of the insulating layer 104 and the conductive layer 105 will be described in more detail hereafter. The electrodes 102 and 103 are connected to a power source (not shown in FIG. 1), and arranged in parallel to each other across the conductive layer 105 so as to provide consistent electrical field distribution therebetween, to ensure optimum matching between the electrodes, the layers (104 and 105) and the substrate 103, and to improve conductivity across the heating element 100.

The insulating layer 104 includes multiple layers of nano-thickness insulating coatings wetted with a surfactant on a ceramic glass surface (the substrate 103) to electrically isolate the conductive coatings (the conductive layer 105) and the ceramic glass (the substrate 103) and prevent detrimental elements migrating from the substrate 103 into the conductive layer 105. It is understood that the insulating layer 104 in this embodiment is optional and in some cases maybe be eliminated.

In this embodiment, the heating material forming the conductive layer 105 includes tin, tungsten, titanium and vanadium with organometallic precursors like Monobutyl Tin Trichloride doped with equal quantities of donor and acceptor elements preferably antimony and zinc at about 3 mol %. The conductive layer 105 is deposited over the insulating coating layers (the insulating layer 105) and the ceramic glass (the substrate 103). The nano-thickness layers of the conductive layer 105 are preferably deposited using spray pyrolysis with controlled temperature and spray movement. For further information, please see U.S. Patent Publication No. 20080190912, now U.S. Pat. No. 8,193,475, which claims priority to U.S. Provisional Application 60/900,994 filed on Feb. 13, 2007, and U.S. Provisional Application 60/990,619 filed on Nov. 28, 2007, all of which are hereby incorporated herein by reference. Other conductive materials and other deposition methods can also be used to produce the heating layers.

The material forming the conductive layer 105 is capable of being applied onto a substrate (the substrate 103) in an open-air environment. The material maintains a stable structure with a low risk of crack formation, and has high conductivity. The material may be of a very low electrical resistance and capable of providing heating and warming over a large area using a direct current (DC) power supply. The material can also maintain its heating performance at high temperatures for prolonged time periods. The material may be deposited in multiple layers on the ceramic glass (the substrate 103) or other suitable materials.

It is noted that the heating element 100 can have different shapes, sizes and/or curvatures since the heating material in the conductive layer 105 is evenly distributed on the insulating layer 104 and the substrate 103. The location of the electrodes may vary as well. For example, the heating element 100 may be circular in shape, with one electrode located around the outer periphery and the other electrode located at the center, forming a bull's eye pattern.

The heating element 100 uses nano-thickness material as the heating material and hence has a fast response and good energy efficiency, and can be precisely controlled. The heating element is of fast heating response and capable to increase heating temperature by up to 5° C. in a second over a large surface area to maximize heating and warming effect.

The nano-thickness material may be non-magnetic and configured for generating heat when driven by a direct current power supply, and does not generate magnetic interference to other medical devices and equipment.

It is noted that the heating element 100 described above may be used in other types of heaters, and its usage is not limited to medical warming systems. For example the heating element 100 may be used in cooktops, hotplates, heaters and defrosters, autoclaves, incubators, portable heaters, home electric baseboard heaters, body warmers, food warmers, bed warmers, home chair warmers, hospitals, nursing homes, room warmers, saunas and/or any other types of heaters.

Figure 2:
FIG. 2 is a high resolution image of a structure that includes a conductive layer of the heating element depicted in FIG. 1.

FIG. 2 is a high resolution image of a structure that includes the conductive layer 105 of the heating element 100 depicted in FIG. 1. Referring to FIG. 2, the view 200 is taken by a high resolution scanning electron microscope and shows the nano-structures of the conductive layer 105.

Figure 3A:
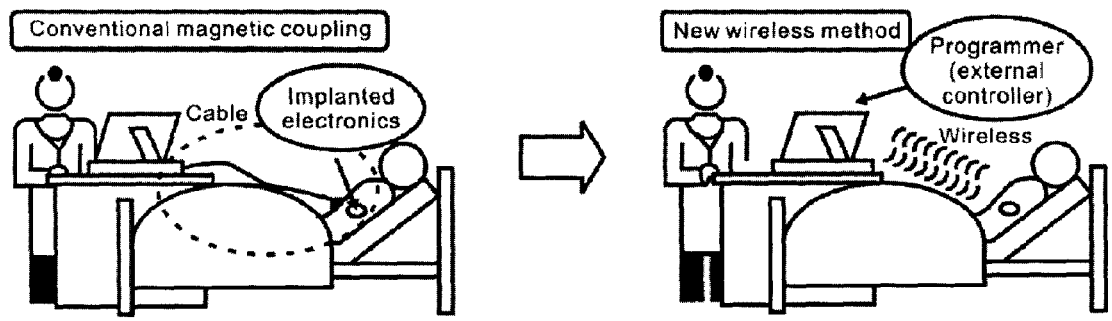
FIG. 3A illustrates wireless communication between a controller and a sensor in the medical warming system depicted in FIG. 1.

FIG. 3A illustrates wireless communication between a controller and a sensor in the medical warming system depicted in FIG. 1. Referring to FIG. 3A, in a conventional medical warming system, sensors and heating elements are attached to human body and both connected to a controller by cables. The controller receives temperature data from the sensors and controls the heating elements through cables. In this embodiment, the communication between the controller and the sensors and the heating elements is conducted wirelessly, which saves the trouble of complicated cable wiring. It is understood, however, that for some patients and under some conditions, for example for patients with a pacemaker, it may still be necessary to use cables in the medical warming system to avoid interference between the medical warming system and other medical devices being used.

Figure 3B:
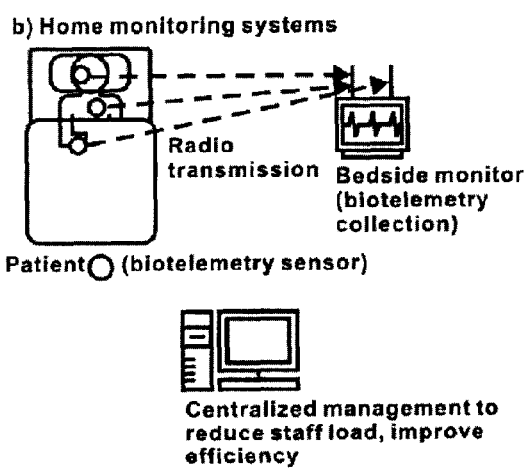
FIG. 3B illustrates the heating process being monitored and controlled by a centralized management system in a medical warming system with a nano-thickness heating element according to another embodiment of the present patent application.

FIG. 3B illustrates the heating process being monitored and controlled by a centralized management system in a medical warming system with a nano-thickness heating element according to another embodiment of the present patent application. Such central management helps to reduce the workload of medical staffs and improve work efficiency. A bedside monitor and control system can be installed to collect temperature data over the different parts of a patient's body.

The temperature data can then be transmitted to a centralized computer management system via networking. Monitoring and controlling of the temperature variations and settings over the body of several patients located at different places become possible by a medical staff staying in a remote control room.

Figure 3C:
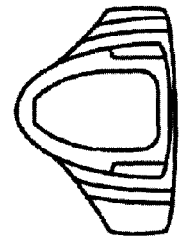
FIG. 3C illustrates a medical warming system with a nano-thickness heating element being integrated with a wearable system according to yet another embodiment of the present patent application.

FIG. 3C illustrates a medical warming system with a nano-thickness heating element being integrated with a wearable system according to yet another embodiment of the present patent application. In this embodiment, with such a system the patient can monitor and control her/his own temperature all by herself/himself. Touch key controls can be used in the wearable system to set the target temperatures. Temperature settings are then transmitted to the nano-thickness heating elements via wireless transmission. The temperature data over the different parts of a patient's body will be transmitted back to the wearable control system to allow appropriate temperature control be achieved. The temperature data and settings will be displayed and monitored through a LCD panel built in the wearable system.

Figure 4:
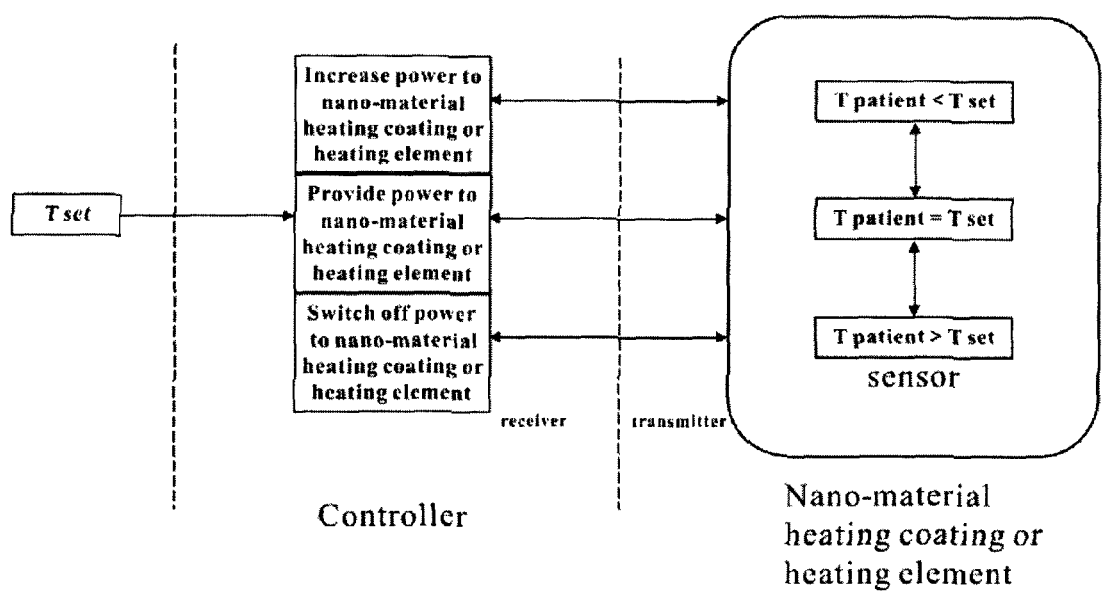
FIG. 4 illustrates the operation of a medical warming system with a nano-thickness heating element according to still another embodiment of the present patent application.

FIG. 4 illustrates the operation of a medical warming system with a nano-thickness heating element according to still another embodiment of the present patent application. Referring to FIG. 4, if the patient is cooler than a desired temperature ($T_{set}$), the controller as illustrated in FIG. 3A is configured to increase the power input to the heating elements and the heating elements of the medical warming system act to raise the temperature of the patient. If the patient's temperature is equal to the desired temperature ($T_{set}$), the controller will keep the power driving the medical warming system as it is and the temperature of the patient stays at $T_{set}$. If the patient's temperature is higher than $T_{set}$, the controller switches off the power driving the medical warming device, the heating elements stop heating the patient and the patient's temperature drops.

The medical warming system in this embodiment includes multiple sensors and multiple heating elements. These sensors and heating elements can be respectively placed at different parts of the patient's body. Individually controlled by a common controller, the sensors and the heating elements can be respectively configured to sense and control the temperature of different parts of the patient's body. For example, a portion of a patient's head may be heated to and maintained at a lower temperature than a portion of the patient's feet. In addition, the heating speed of each heating element is also controlled by the controller. For example, in one case, the heating process may be relatively rapid and the desired temperature is achieved within one minute. In another case, the heating process may be relatively gradual and take ten minutes to complete.

In this embodiment, the controller includes a receiver and the sensors respectively include a transmitter. The sensors sense temperature of different parts of a patient's body and transmit the temperature data to the controller through the transmitters. The temperature data is received by the controller through the receiver. As described in more detail hereafter, the receiver and the transmitters can be wireless receiver and wireless transmitters.

Figure 5:
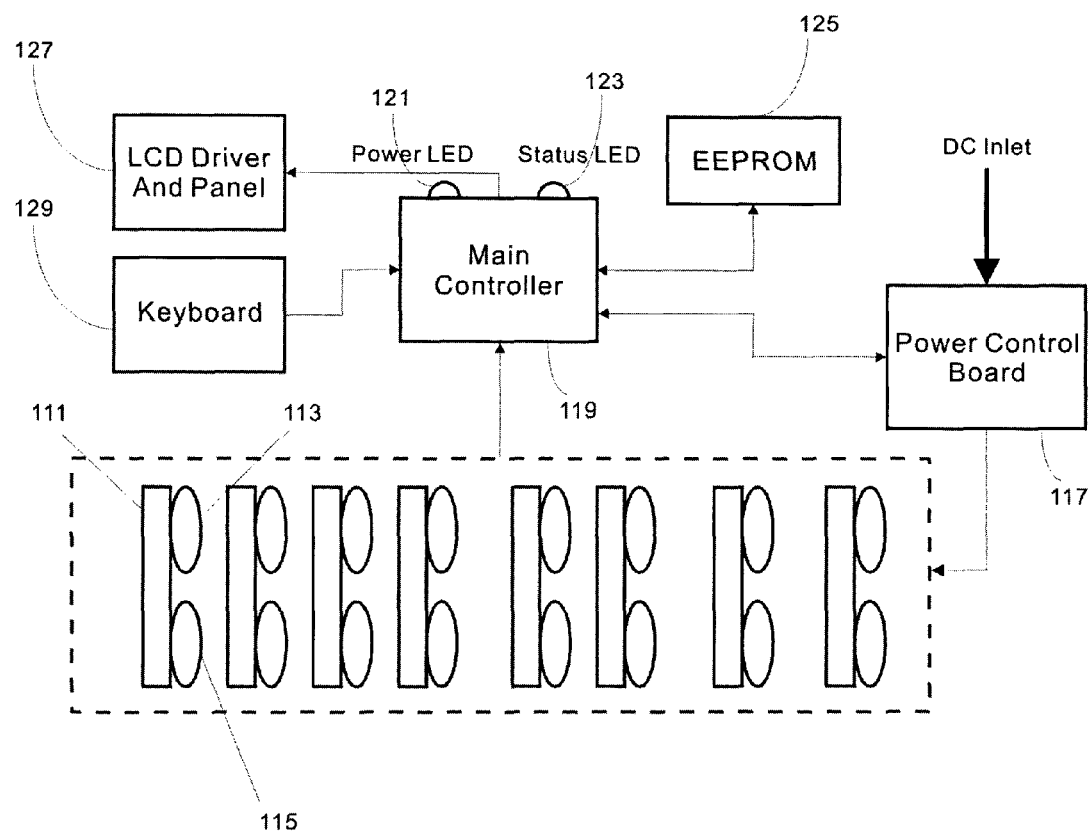
FIG. 5 illustrates a block diagram of a medical warming system with a nano-thickness heating element according to still another embodiment of the present patent application.

FIG. 5 illustrates a block diagram of a medical warming system with a nano-thickness heating element according to still another embodiment of the present patent application. Referring to FIG. 5, the system includes a plurality of heating elements 111 being placed close to different parts of a patient's body, a first group of temperature sensors 113 disposed close to the heating elements 111 and configured for sensing the temperatures of the heating elements 111, a second group of temperature sensors 115 disposed closed to different parts of the patient's body and configured for sensing the temperatures of the different parts of the patient's body, a power control board 117 connected with the heating elements 111 and configured for controlling the electric power driving the heating elements 111, and a controller 119 being connected with the power control board 117 and in communication with the temperature sensors 113 and 115. The controller 119 is configured for receiving temperature data from the temperature sensors 113 and 115 and accordingly controlling the power control board 117 to adjust the electric power driving the heating elements 111. The controller 119 is an intelligent power monitor and control device that includes an ADC (analog-to-digital converter) and PWM (pulse-width modulation) driver to achieve accurate temperature control, to smooth the power delivery to the heating elements 111 and to optimize their heating performance and power efficiency. It is noted that the heating elements 111 in this embodiments are the same as the heating element illustrated in FIG. 1A and FIG. 1B.

Referring to FIG. 5, in this embodiment, the system further includes a power indicator, such as a LED (light emitting diode) 121, for indicating the on/off status of the electric power supplied to the system, a status indicator, such as a LED 123, for indicating the operating status of the system, a display module, such as a LCD (liquid crystal display) module 127, for displaying interactive information to an operator, an input device, such as a keyboard 129, for the operator to input information to the system, and a storage module for storing operation data and equipment settings (also known as "profiles") of the system for operating the system at different patients and/or under different conditions. In this embodiment, the LCD module includes a LCD panel and a LCD driver driving the LCD panel. The storage module 125 is an EEPROM (Electrically Erasable Programmable Read-Only Memory).

The communication between the temperature sensors 113, 115 and the main multipoint controller 119 can be wired communication or wireless communication complying with protocols such as Bluetooth, Zigbee, and etc. Each temperature sensor 113 or 115 includes a wired and/or wireless transmitter. The controller 119 includes a wired and/or wireless receiver and is configured to analyze the temperature data received from the temperature sensors 113 and 115 and adjust the electric power driving the heating elements 111 until the patient's temperature reaches a target temperature within ±0.5° C. Each temperature sensor 113 or 115 includes a plurality of sensors, which may include a working sensor or a main sensor for measuring the temperature of the patient's body or the heating elements 111, and a reference sensor or a backup sensor. The controller 119 receives measurements from both sensors. If there is a difference between the readings of the two sensors, at least one of the working sensor and the reference sensor may be malfunctioning, for example, being defective, or coming loose from the patient. In such case, a technician, the patient, or the operator, may be prompted to inspect the temperature sensor, and to reattach or replace it if necessary. When a difference is detected, the controller 119 is configured to shut off the power driving the heating elements 111 until the temperature sensor is fixed or replaced. It is understood that the above monitoring process is described only as an example and the controller 119 can execute other preset diagnostic routines for monitoring the operating status of the system. Hence, in this embodiment, the medical warming system is a multipoint temperature control system for medical use with a nano-thickness heating element that is capable of individually controlling the temperature of different parts of the patient to stay at various preset target temperature values with relatively high accuracy and fast response.

Figure 6:
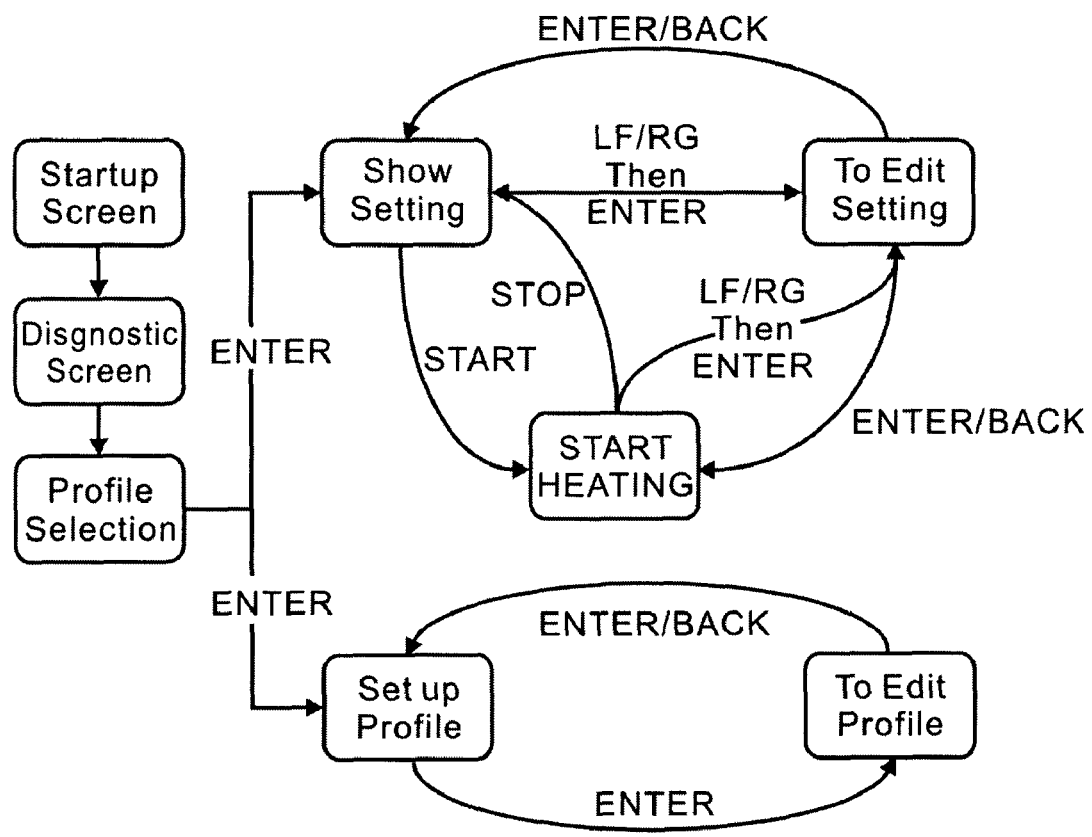
FIG. 6 illustrates an operation flow of the medical warming system with a nano-thickness heating element depicted in FIG. 5.

FIG. 6 illustrates an operation flow of the medical warming system with a nano-thickness heating element depicted in FIG. 5. Referring to FIG. 6, a startup screen is displayed when the system is powered on, followed by a diagnostic screen showing the result of a diagnostic process to ensure normal operation of the warming system. Then the settings of the system are displayed and an operator can edit the settings as he or she sees appropriate for the specific patient and/or the specific medical procedure. It is understood that such settings may include a desired target temperature for a specific part of a patient's body. After the operator confirms the settings are set correctly, the operator can start the heating process with the settings. As mentioned above, particular settings for certain types of patients and/or medical procedures can be saved in the storage module beforehand as "profiles." The operator has an option to load a specific profile or edit a profile after the diagnostic screen is displayed.

Figure 7:
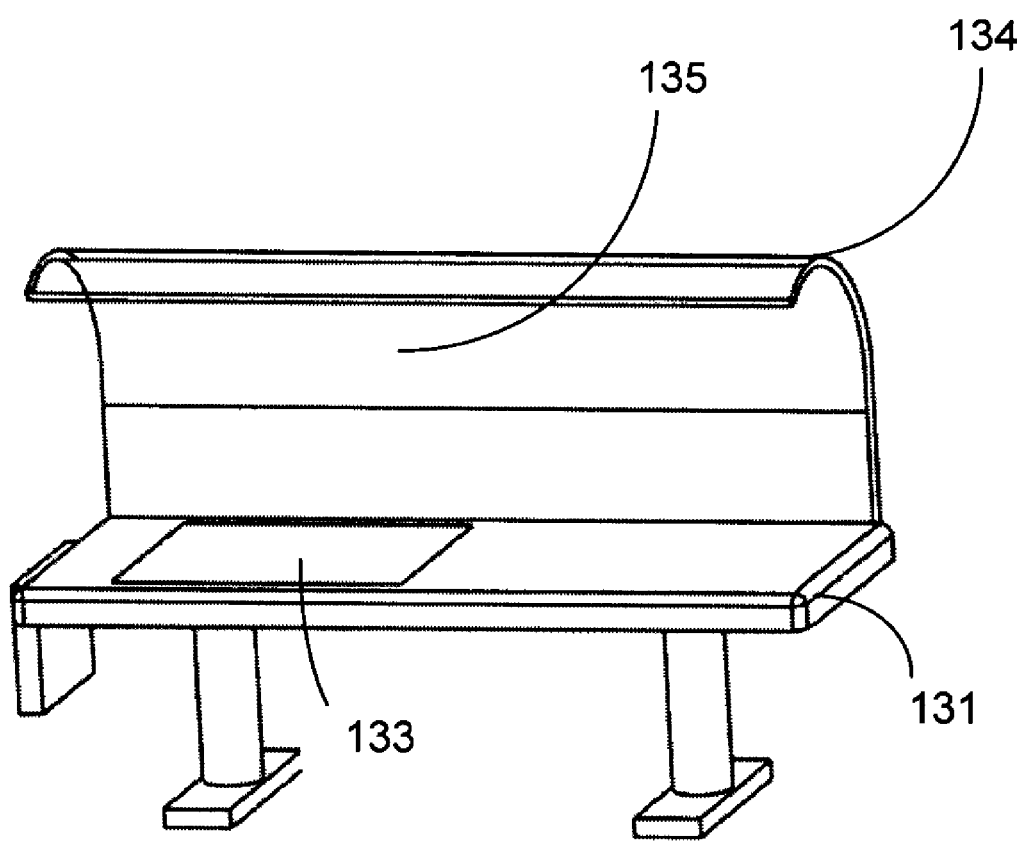
FIG. 7 illustrates an arrangement of heating elements in a medical warming system according to still another embodiment of the present patent application.

FIG. 7 illustrates an arrangement of heating elements in a medical warming system according to still another embodiment of the present patent application. Referring to FIG. 7, the medical warming system further includes a platform 131. The platform 131 can be a surgery table or a bed. A first heating element 133 is disposed on the bed 131 and a second heating element 135 is disposed on a curved panel 134 that is connected to the bed 131. The panel 134 can be closed to cover the bed 131 when a patient is lying on the bed 131. The first heating element 133 can be moved on the bed 131 and fixed on a desired position. The temperature of the heating elements 133 and 135 can be individually controlled by the system. Comparing with the second heating element 135, the first heating element 133 is in more intimate contact with the patient and configured to transfer heat to the patient through heat conduction. The second heating element 135 is configured to transfer heat to the patient through heat conduction and/or radiation. The first heating element 133 may be controlled to have a lower temperature than the second heating element 135 to avoid burning the patient. The heat elements 133 and 135 are respectively controlled by a controller as illustrated in FIG. 5 according to the temperature of the patient sensed by the above-mentioned temperature sensors and the target temperatures. It is understood that there may be more or fewer heating elements. For example, there may be a plurality of heating elements located on the bed 131, each of which is capable of being individually controlled by the controller according to the desired heating conditions.

In operation, an operator can select target temperatures for the medical warming system. A controller as illustrated in FIG. 5 controls the electrical power to the heating elements according to the target temperatures. The temperature of different parts of the patient's body is monitored by the wired or wireless temperature sensors on the patient's body. The temperature sensors transmit signals from different parts of the patient's body to the controller. The controller receives signals from both the sensors on the patient's body and the sensors on the heating elements of the medical warming system. Analysis of the temperature data will be made by the controller to determine the power provided to the heating elements so as to achieve the target temperatures at the different parts of the patient's body. If the temperature of a part of the patient's body is higher than the target temperature for that part, the controller reduces or shuts off the electrical power provided to the corresponding heating element. If the temperature of the patient no longer exceeds the target temperature, the controller maintains or increases the amount of electrical power provided to the heating elements to maintain that part of the patient's body at the target temperature. If the temperature of a part of the patient's body is below the target temperature, the controller increases the electrical power provided to the corresponding heating element with a fast response. If the temperature of the patient is no longer below the target temperature, the controller maintains or reduces the electrical power electrical power provided to the heating elements to maintain the patient's body at the target temperature.

Figure 8:
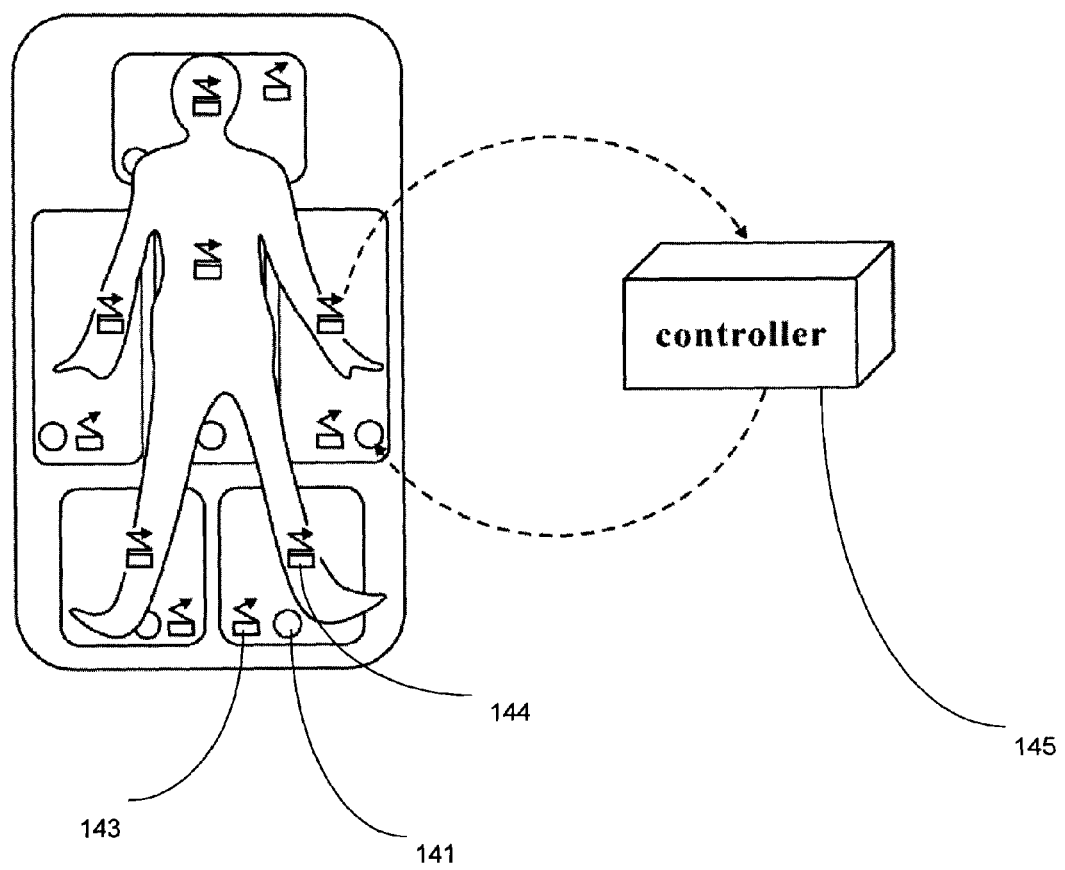
FIG. 8 illustrates another arrangement of heating elements in a medical warming system according to still another embodiment of the present patent application.

FIG. 8 illustrates another arrangement of heating elements in a medical warming system according to still another embodiment of the present patent application. In this embodiment, the temperature sensors 143 are disposed close to the heating elements 141 and configured for sensing the temperature thereof. The temperature sensors 144 are disposed close to different parts of the patient's body and configured for sensing the temperature thereof. Each of the heating elements 141 can be individually controlled by a controller 145, which receives temperature data from the temperature sensors 143 and 144 and process the data. In other words, some of the heating elements 141 may be turned on while others are turned off. Some of the heating elements 141 may be set to a first temperature while others are set to a second temperature. Each heating element 141 may be individually set to a specific temperature. Some of the heating elements 141 may be set to rapidly heat up while others are set to slowly heat up if needed.

Figure 9:
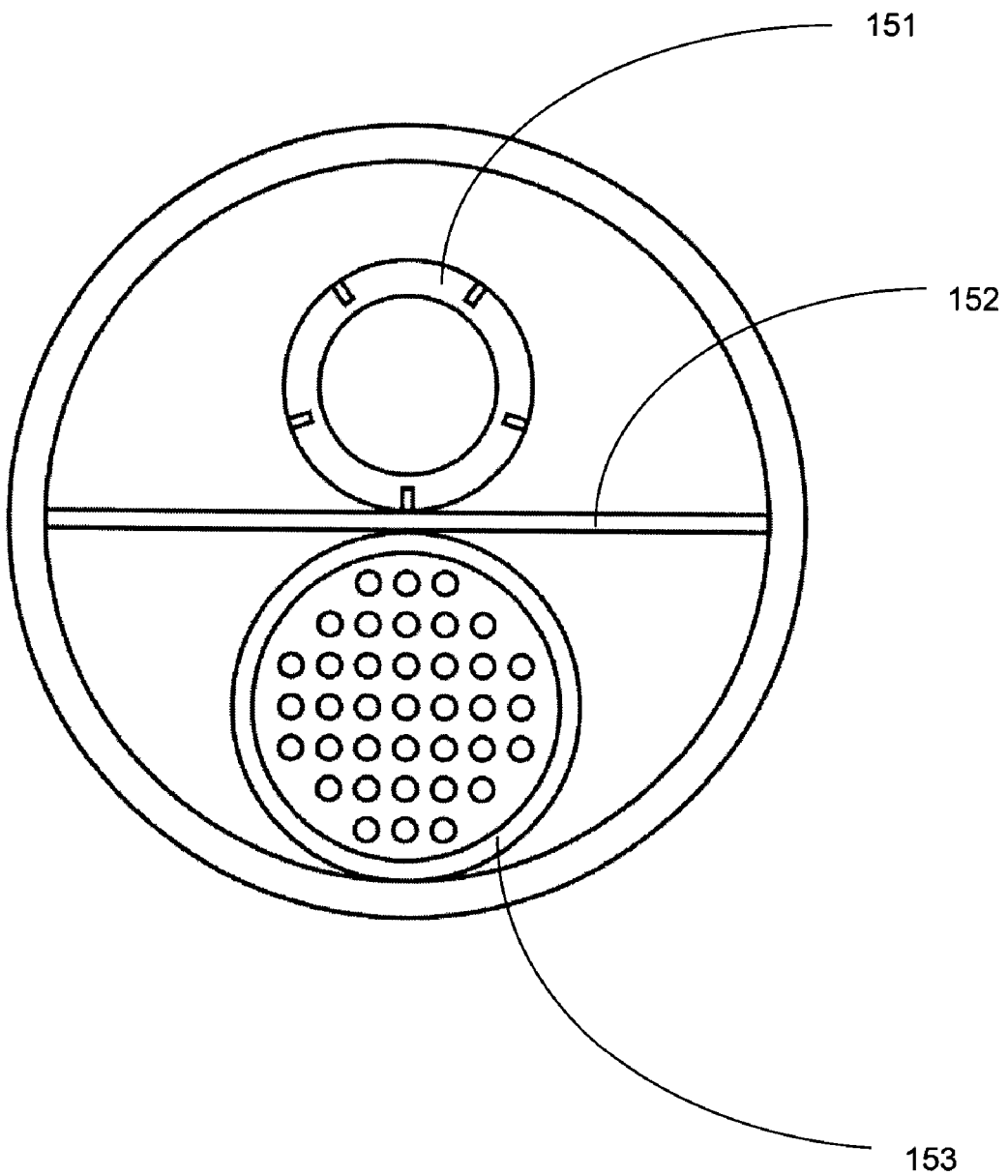
FIG. 9 shows a general setup for magnetic resonance imaging test for a medical warming system with a nano-thickness heating element according to still another embodiment of the present patent application.
Figure 10:
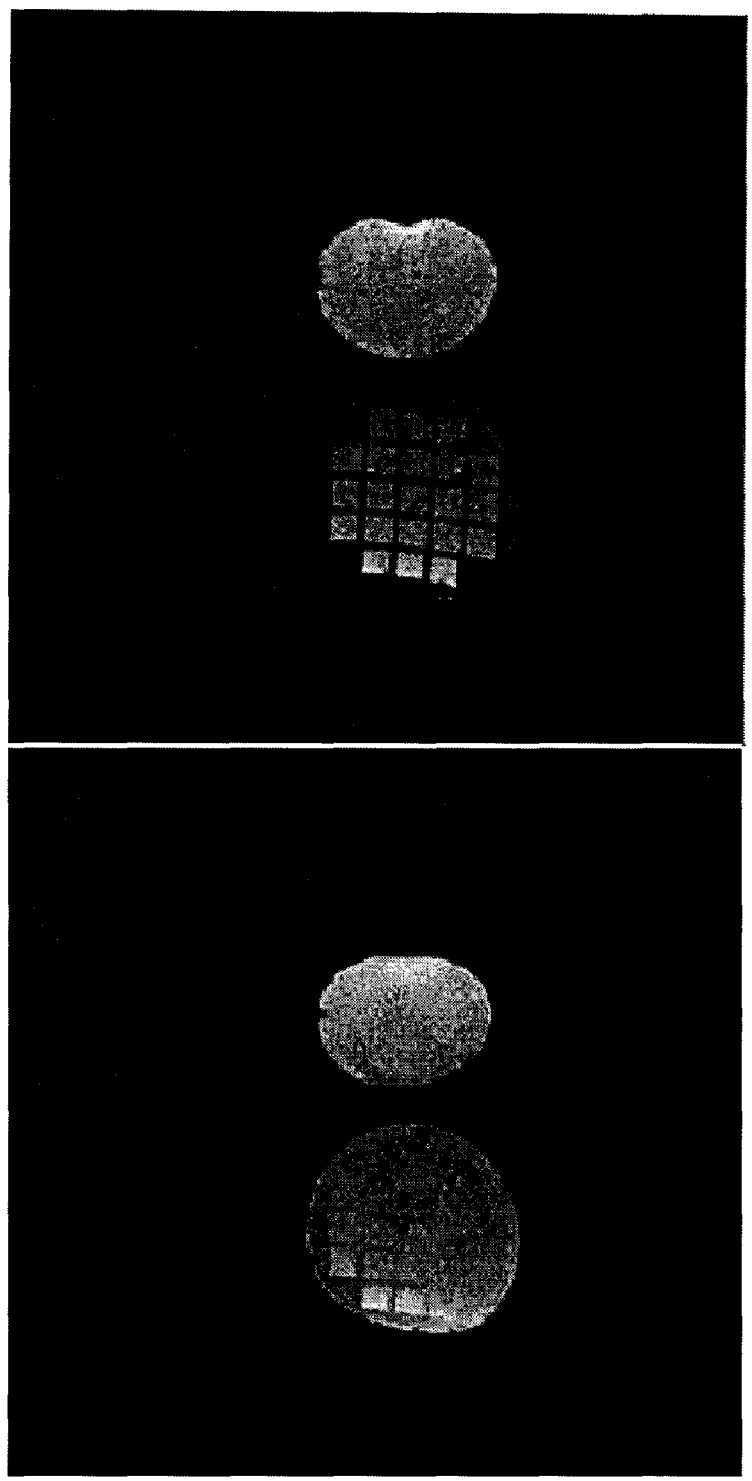
FIG. 10 shows two scan images taken at 0.3T in the magnetic resonance imaging test illustrated in FIG. 9.
Figure 11:
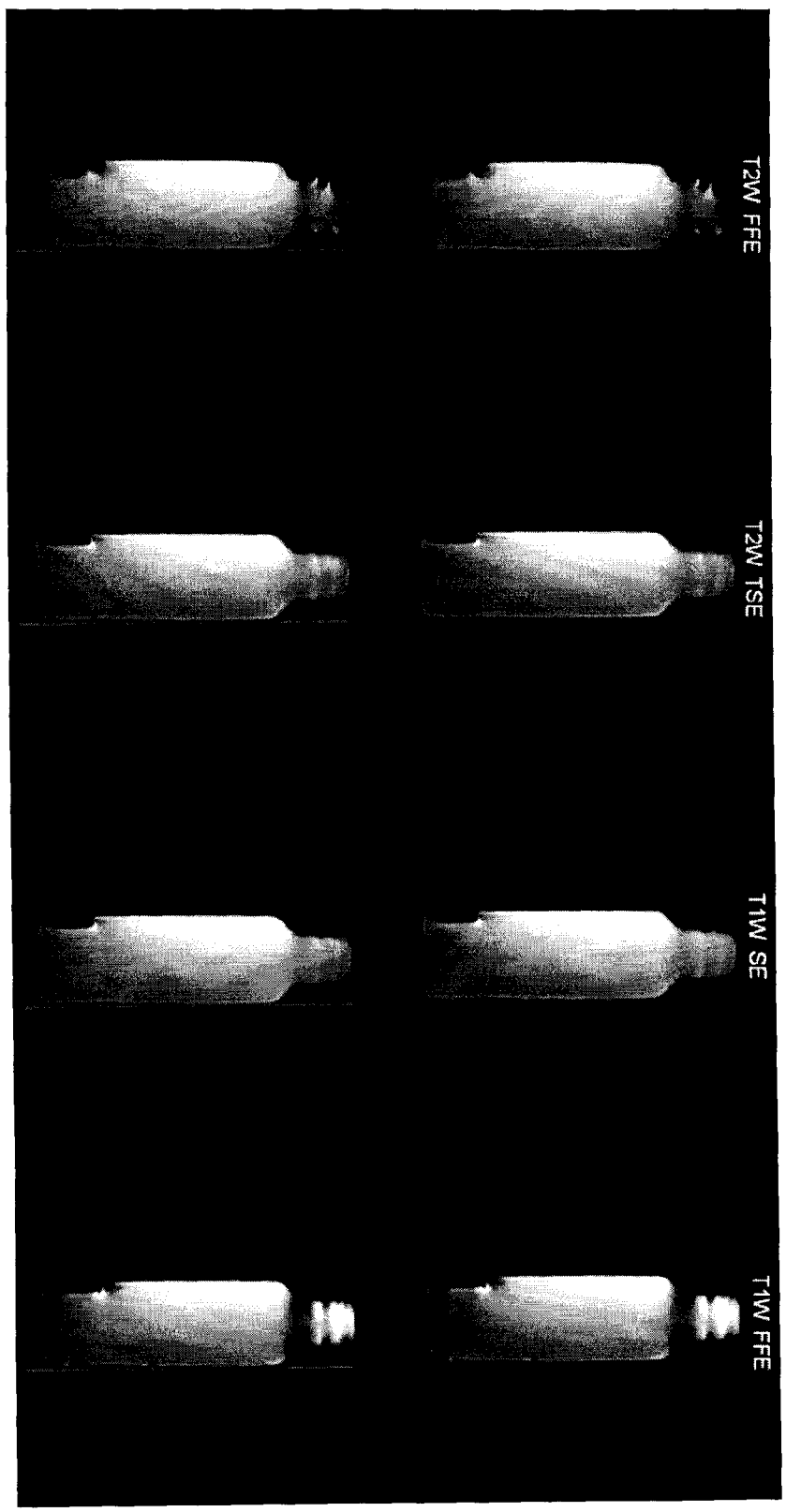
FIG. 11 shows four scan images taken at 3T in the magnetic resonance imaging test illustrated in FIG. 9 at different resonance frequencies.

In magnetic resonance imaging (MRI), it is desired to have a system to provide proper warmth to the patient without generating interference to the magnetic resonance imaging. A MRI test confirms that a medical warming system with a nano-thickness heating element according to still another embodiment of the present patent application is MRI compatible. FIG. 9 shows a general setup for magnetic resonance imaging test for a medical warming system with a nano-thickness heating element according to still another embodiment of the present patent application. Referring to FIG. 9, a plastic bottle 151 filled with water is placed above a heating element 152, which includes multilayered nano-thickness heating material applied on a ceramic glass as illustrated in FIG. 1A. A phantom 153 was also placed under the heating element 152 so as to locate the position of the heating element 152 on the scan images to be taken. MRI uses a powerful magnetic field to align the nuclear magnetization of hydrogen atoms in water (in human body), and so the image of the heating element does not appear in the MRI test. FIG. 10 shows two scan images taken at 0.3 T in the magnetic resonance imaging test illustrated in FIG. 9. FIG. 11 shows four scan images taken at 3 T in the magnetic resonance imaging test illustrated in FIG. 9 at different resonance frequencies. Referring to FIG. 10 and FIG. 11, no sign of interference or artifact in the image is shown in both low field (0.3 T, T: tesla) and high field (3 T) magnetic resonance imaging. The dark spots in the images of the water bottle are formed by reflections by some air trapped inside the bottle, which is not fully filled at the first place. Absence of artifacts in the images under both low field and high field MRI tests indicates that the medical warming system in this embodiment is MRI compatible. The reason for such compatibility lies in that unlike other conventional heating devices, the non-magnetic nano-thickness heating material of the heating element 152 used in the medical warming system in this embodiment does not induce magnetic field and generate interference to other medical devices. This capacity, together with the fast heating response and high accuracy temperature control, provides a huge potential for the medical warming system in this embodiment to perform heating and warming functions in many medical and thermal therapy applications that cannot be achieved by other heating systems or devices.

The medical warming systems provided by the above embodiments can be used to provide supplemental heating to a person for medical purposes at institutional locations such as schools, hospitals, nursing homes, retirement homes, and residential homes. The medical warming systems may be used for animals as well as for humans. For example, the medical warming systems may be used to help reduce pain associated with arthritis for a family pet. The system may be disposed at the animal's sleeping location or other locations frequently visited by the animal.

The medical warming systems provided by the above embodiments can operate to minimize temperature shocks. For example, a personal medical warmer in accordance with the embodiments can be issued to first aid workers and be used to warm injured patients, thereby minimizing the problems of temperature shocks. Such a warmer can use a battery as its electrical power supply, or alternatively, be connected to a power source provided by a vehicle. The good power efficiency of the nano-thickness heating material in the heating elements is particularly suitable for uses without grid-based power supplies.

While the present patent application has been shown and described with particular references to a number of embodiments thereof, it should be noted that various other changes or modifications may be made without departing from the scope of the present invention.

What is claimed is:

1. A medical warming system comprising: a plurality of heating elements respectively adapted to be disposed close to various parts of a patient's body, each heating element comprising a multi-layer conductive coating of about 50 nm to about 70 nm each layer in thickness; a first group of sensors disposed at the proximity of the heating elements and configured for measuring the temperatures of the heating elements; a second group of sensors adapted to be disposed at the various parts of the patient's body and configured for measuring the temperatures of the various parts of the patient's body; a power control board connected with the heating elements and configured for controlling the electric power driving the heating elements; and a controller being connected with the power control board and in communication with the first group and the second group of sensors, the controller being configured for receiving temperature data from the sensors and controlling the power control board to adjust the electric power driving the heating elements accordingly; wherein each sensor in the first group and the second groups of sensors comprises a working sensor and a reference sensor, and the controller is configured to compare the readings from the working sensor and the reference sensor and thereby to determine whether the sensor is working properly; the conductive coating is deposited using spray pyrolysis; and the conductive coating includes tin, tungsten, titanium and vanadium.

2. The medical warming system of claim 1, wherein the controller is configured to control the power control board to individually adjust the electric power provided to each heating element independently from each other.

3. The medical warming system of claim 2, wherein the controller is configured to control the temperature of each heating element according to a predetermined target temperature and the temperature of a corresponding part of the patient's body that is measured by a corresponding sensor in the second group of sensors adapted to be disposed at the proximity of the corresponding part of the patient's body.

4. The medical warming system of claim 3, wherein the controller is configured to increase the electric power provided to a heating element if the temperature of the corresponding part of the patient's body is lower than the target temperature, to reduce the electric power provided to the heating element if the temperature of the corresponding part of the patient's body is higher than the target temperature, and to maintain the electric power provided to the heating element if the temperature of the corresponding part of the patient's body is equal to the target temperature.

5. The medical warming system of claim 1, wherein the spray pyrolysis is carried out at a temperature of about 650° C. to about 750° C., at a spray pressure of about 0.4 MPa to about 0.7 MPa, at a spray head speed of less than 1000 mm per second, and by alternating spray passes in a direction of about 90 degrees to each other.

6. A medical warming system comprising: a plurality of heating elements respectively adapted to be disposed close to various parts of a patient's body, each heating element comprising a multi-layer conductive coating of about 50 nm to about 70 nm each layer in thickness; a first group of sensors disposed at the proximity of the heating elements and configured for measuring the temperatures of the heating elements; a second group of sensors adapted to be disposed at the various parts of the patient's body and configured for measuring the temperatures of the various parts of the patient's body; and a controller being in communication with the first group and the second group of sensors, the controller being configured to control the temperature of each heating element according to a predetermined target temperature and the temperature of a corresponding part of the patient's body that is measured by a corresponding sensor in the second group of sensors adapted to be disposed at the proximity of the corresponding part of the patient's body; the conductive coating is deposited using spray pyrolysis; and the conductive coating includes tin, tungsten, titanium and vanadium.

7. The medical warming system of claim 6, wherein the controller is configured to individually adjust the electric power provided to each heating element independently from each other.

8. The medical warming system of claim 6, wherein the controller is configured to increase the electric power provided to a heating element if the temperature of the corresponding part of the patient's body is lower than the target temperature, to reduce the electric power provided to the heating element if the temperature of the corresponding part of the patient's body is higher than the target temperature, and to maintain the electric power provided to the heating element if the temperature of the corresponding part of the patient's body is equal to the target temperature.

9. The medical warming system of claim 6, wherein each sensor in the first group and the second groups of sensors comprises a working sensor and a reference sensor, and the controller is configured to compare the readings from the working sensor and the reference sensor and thereby to determine whether the sensor is working properly.

10. The medical warming system of claim 6, wherein the controller is configured to control the rate of temperature increase of each heating element according to a predetermined setting.

11. The medical warming system of claim 6 further comprising a storage module, the storage module being configured for storing settings of the system for operating the system at particular patients or under particular conditions, the controller being configured to load system settings from the storage module and control the heating elements according to the settings.

12. The medical warming system of claim 6, wherein the spray pyrolysis is carried out at a temperature of about 650° C. to about 750° C., at a spray pressure of about 0.4 MPa to about 0.7 MPa, at a spray head speed of less than 1000 mm per second, and by alternating spray passes in a direction of about 90 degrees to each other.

13. A medical warming system comprising: a plurality of heating elements respectively adapted to be disposed close to various parts of a plurality of patients' bodies, each heating element comprising a multi-layer conductive coating of about 50 nm to about 70 nm each layer in thickness; a first group of sensors disposed at the proximity of the heating elements and configured for measuring the temperatures of the heating elements; a second group of sensors adapted to be disposed at the various parts of the patients' bodies and configured for measuring the temperatures of the various parts of the patients' bodies; and a controller being in communication with the first group and the second group of sensors, the controller being configured for receiving temperature data from the sensors and controlling the temperature of each heating element accordingly; the conductive coating is deposited using spray pyrolysis; and the conductive coating includes tin, tungsten, titanium and vanadium.

14. The medical warming system of claim 13, further comprising a power control board being in communication with the heating elements and configured for controlling the electric power driving the heating elements, wherein the controller is configured to control the power control board to individually adjust the electric power provided to each heating element independently from each other.

15. The medical warming system of claim 14, wherein the controller is configured to control the temperature of each heating element according to a predetermined target temperature and the temperature of a corresponding part of the patient's body that is measured by a corresponding sensor in the second group of sensors disposed at the proximity of the corresponding part of the patient's body.

16. The medical warming system of claim 15, wherein the controller is configured to increase the electric power provided to a heating element if the temperature of the corresponding part of the patient's body is lower than the target temperature, to reduce the electric power provided to the heating element if the temperature of the corresponding part of the patient's body is higher than the target temperature, and to maintain the electric power provided to the heating element if the temperature of the corresponding part of the patient's body is equal to the target temperature.

17. The medical warming system of claim 13, wherein the controller is physically located at a centralized location, and the heating elements, the first group of sensors and the second group of sensors are located remotely to the centralized location.

18. The medical warming system of claim 13, wherein the controller is configured to control the rate of temperature increase of each heating element according to a predetermined setting.

19. The medical warming system of claim 13 further comprising a storage module, the storage module being configured for storing settings of the system for operating the system at particular patients or under particular conditions, the controller being configured to load system settings from the storage module and control the heating elements according to the settings.

20. The medical warming system of claim 13, wherein each sensor in the first group and the second groups of sensors comprises a working sensor and a reference sensor, and the controller is configured to compare the readings from the working sensor and the reference sensor and thereby to determine whether the sensor is working properly.

21. The medical warming system of claim 13, wherein the spray pyrolysis is carried out at a temperature of about 650° C. to about 750° C., at a spray pressure of about 0.4 MPa to about 0.7 MPa, at a spray head speed of less than 1000 mm per second, and by alternating spray passes in a direction of about 90 degrees to each other.

* * * * *